United States Patent [19]

Munson, Jr. et al.

[11] Patent Number: 5,137,895
[45] Date of Patent: Aug. 11, 1992

[54] 3-[N-AROYL(OR THIOAROYL)AMINOMETHYL]-3-QUINUCLIDINOLS

[75] Inventors: Harry R. Munson, Jr., Leawood, Kans.; Gunnar E. Jagdmann, Jr., Apex, N.C.

[73] Assignee: A. H. Robins Company, Incorporated, Richmond, Va.

[21] Appl. No.: 692,582

[22] Filed: Apr. 29, 1991

[51] Int. Cl.$^5$ ................. C07D 453/02; A61K 31/435
[52] U.S. Cl. .................................... 514/305; 546/137
[58] Field of Search ...................... 546/137; 514/305; 536/17.2, 17.6, 17.9, 18.3, 18.4

[56] References Cited

U.S. PATENT DOCUMENTS 4,593,034  6/1986  Munson, Jr. et al. .............. 514/305

FOREIGN PATENT DOCUMENTS 0221702 10/1986 European Pat. Off. .

Primary Examiner—C. Warren Ivy
Assistant Examiner—Catherine Scalzo
Attorney, Agent, or Firm—George Tarnowski

[57] ABSTRACT

3-[N-Aroyl(or thioaryol)aminoalkyl]-3-quinuclidinols corresponding to the formula:

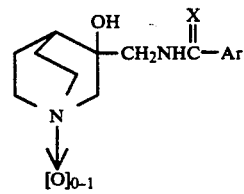

wherein X is O or S, and Ar is phenyl, substituted phenyl, indole, indazole or pyrimidine; optical isomers and the pharmaceutically acceptable acid addition salts and solvates thereof. These compounds have gastric emptying, antiemetic, anxiolytic and selective serotonin modulating or inhibiting activity.

13 Claims, No Drawings

3-[N-AROYL(OR THIOAROYL)AMINOMETHYL]-3-QUINUCLIDINOLS

FIELD OF INVENTION

The present invention relates to novel 3-[N-aroyl (or thioaroyl)aminomethyl]-1-azabicyclo[2.2.2]octan-3-ols which may also be referred to as 3-[N-aroyl (or thioaroyl)aminomethyl]-3-quinuclidinols. Compounds of the present invention have gastric emptying, antiemetic, anxiolytic, antiarrhythmic, and selective serotonin modulation or inhibition properties. This invention also relates to pharmaceutical compositions containing these compounds.

BACKGROUND OF THE INVENTION

A search of the scientific literature has not revealed the 3-[N-aroyl (or thioaroyl-)aminomethyl]-3-quinuclidinols of this invention.

Certain 3-hydroxy-3-aminomethylquinuclidines used in preparation of the compounds are disclosed in U.S. Pat. No. 3,775,418.

Compounds having limited resemblance to those of the present invention in structure but having no hydroxy substitution on the quinuclidine moiety and no interposing methylene group are disclosed in U.S. Pat. Nos. 4,593,034; 4,722,834 and 4,657,911 as exemplified by the following composite structure:

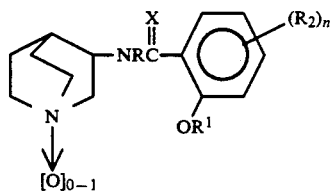

The compounds are useful in increasing gastric motility and for controlling certain types of emesis.

An application disclosing antianxiety utility for the compounds essentially those of U.S. Pat. No. 4,593,034 described above has been filed in Great Britain (U.K. application 8629962 filed Dec. 16, 1986) and in the U.S. (U.S. application Ser. No. 133,410 filed Dec. 15, 1987 now U.S. Pat. No. 4,908,370).

A group of compounds also having limited resemblance to the compounds of present invention having an interposing methylene group but having no hydroxy substitution on the quinuclidine moiety are disclosed in E.P. 0221702A2. The compounds have the formula:

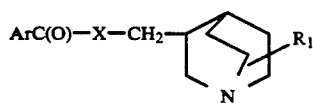

wherein X is NH or O and $R^1$ is H, alkyl, phenyl or phenylalkyl and are said to have activity as gastric motility enhancers, antiemetics and as serotonin antagonists.

SUMMARY OF THE INVENTION

The novel 3-[N-aroyl (or thioaroyl-)aminomethyl]-1-azabicyclo[2.2.2]octan-3-ols of this invention useful in the therapeutic methods and pharmaceutical compositions herein have the formula:

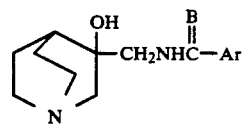

wherein B is O or S and Ar is selected from:

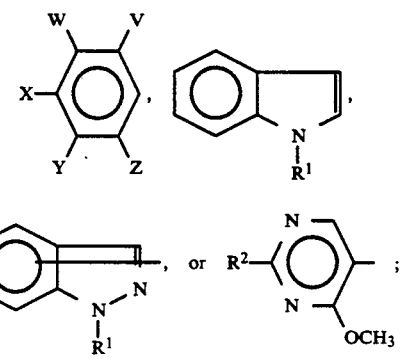

and $R^1$ is H or loweralkyl;
$R^2$ is amino, loweralkylamino, or diloweralkylamino;
V is selected from hydrogen, hydroxy, $-OR^3$, $-SR^3$ or halogen;
W is selected from hydrogen and $-OR^3$
X is selected from hydrogen, amino, loweralkylamino, diloweralkylamino, loweralkylcarbonylamino, loweralkylsulfonylamino, or $-OR^3$;
Y is selected from hydrogen, halogen, halogen, or $-OR^3$;
Z is selected from hydrogen, halogen, or $-OR^3$;
$R^3$ is selected from loweralkyl, loweralkoxyloweralkyl, loweralkylthioloweralkyl, loweralkylsulfinylloweralkyl, loweralkylsulfonylloweralkyl, loweralkenyl, 2-tetrahydropyranylmethyl, diloweralkylaminocarbonylloweralkyl, substituted benzyl; the optical isomers; the N-oxide and the pharmaceutically acceptable salts thereof.

In the further definition of symbols in the formulas hereof and where they appear elsewhere throughout this specification and the claims, the terms have the following significance.

The term "loweralkyl" as used herein includes straight and branched chain radicals of up to four carbons inclusive and is exemplified by such groups as methyl, ethyl, propyl, isopropyl, butyl, isobutyl, and t-butyl. The term "loweralkoxy" has the formula -O-loweralkyl.

The term loweralkenyl includes straight and branched chain alkene radicals of from 2 to 4 carbons inclusive is exemplified by such groups as vinyl, propylene, butylene and isobutylene.

The term "aroyl" refers to an Ar group under the definition of Formula I in conjunction with a carbonyl moiety and the term thioaroyl refers similarly to the Ar group with a thioxo group

When in the instance that phenyl is substituted by highly branched alkyl or alkenyl radicals such as t-butyl or isobutenyl, no more than two such groups are anticipated to be present on any one phenyl group and when lower alkyl groups are contemplated in the 2 and 6 position of phenyl, only one such highly branched group may be present, steric hinderance to preparation being one consideration.

The terms "halo" or "halogen" when referred to herein include fluorine, chlorine, bromine and iodine unless otherwise stated.

"Pharmaceutically acceptable acid addition salts" include the acid addition salts, hydrates, alcoholates and quaternary salts of the compounds of Formula I which are physiologically compatible in warm blooded animals. The acid addition salts may be formed by either strong or weak acids. Representative of strong acids are hydrochloric, sulfuric and phosphoric acids. Representative of weak acids are fumaric, maleic, succinic, oxalic, citric, tartaric, cyclohexamic and the like.

Compounds which enhance gastric emptying are useful in treating delayed gastric emptying, indigestion, flatulence, esophageal reflux and peptic ulcer. Compounds of this invention having antiemetic activity are useful in treating emesis and emesis caused by radiation or cancer chemotherapy with platinum and non-platinum chemotherapeutic agents. Compounds of this invention useful in modulating or inhibiting selective actions of serotonin are useful in the treatment of migraine, cluster headaches or trigeminal neuralgia. Compounds which modulate or inhibit serotonin may also be of potential in treating psychoses, arrhythmias, and irritable bowel syndrome.

It is therefore a primary object to provide novel 3-[N-aroyl (or thioaroyl)aminomethyl]-1-azabicyclo[2.2.2]octan-3-ols.

Another object is to provide methods of treating gastric stasis, emesis, anxiety and to inhibit or modulate certain actions of serotonin (5-HT) and provide treatment for these disorders in living animals using the novel 3-[N-aroyl (or thioaroyl)aminomethyl]-1-azabicyclo[2.2.2]octan-3-ols.

An additional object is to provide means of controlling emetic episodes due to administration of platinum and other anticancer drugs and emesis due to radiation.

A further object is to provide pharmaceutical compositions containing the novel 3-[N-aroyl (or thioaroyl)aminomethyl]-1-azabicyclo[2.2.2]octan-3-ols.

Additional objects will become apparent to one skilled in the art and still others will become apparent hereinafter.

DETAILED DESCRIPTION OF THE INVENTION

Preparation of 3-(N-aroylaminomethyl)-1-azabicyclo[2.2.2]octan-3-ols.

The non-oxidized compounds of Formula I, i.e., compounds wherein the quinuclidine nitrogen has not been converted to the oxide, may be prepared by reacting a suitably substituted arylcarboxylic acid or arylcarboxylic acid halide with 3-aminomethyl-3-quinuclidinol (3-aminomethyl-1-azabicyclo[2.2.2]octan-3-ol) (II) by general methods known in the art as illustrated in the following Methods A, B, C and D wherein Ar is defined under Formula I hereinabove.

METHOD A

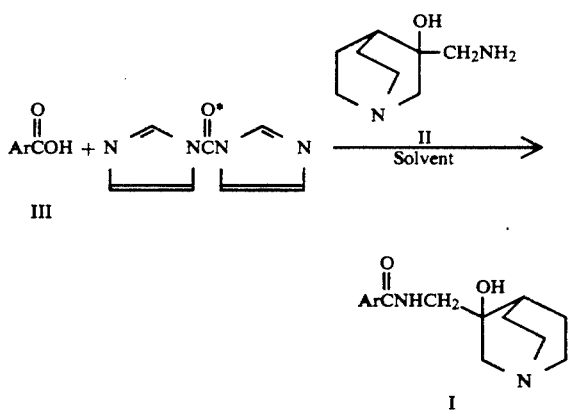

*oxygen may be substituted by sulfur

Equimolar quantities of the arylcarboxylic acid (III) and 1,1'-carbonyldiimidazole are stirred together in a suitable dry aprotic solvent for a suitable period and 3-aminomethyl-1-azabicyclo[2.2.2]octan-3-ol is added to the reaction mixture and the reaction mixture stirred with or without heating until the reaction is completed.

METHOD B

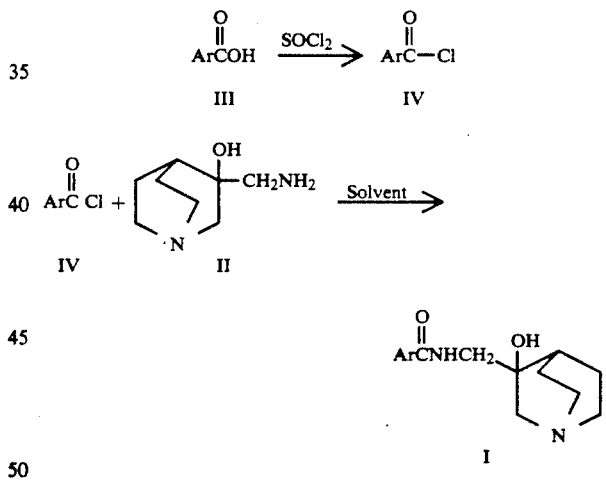

Aryl carboxylic acids (III) bearing no interfering substituents, such as reactive hydroxyl or amino groups or where such groups have removable protecting groups can be converted into the arylcarbonyl chlorides (IV) by known procedures. The arylcarbonyl chloride is reacted with an equivalent amount of 3-aminomethyl-1-azabicyclo[2.2.2]octan-3-ol (II) in an appropriate aprotic solvent to yield the product.

METHOD C

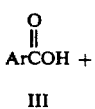

III

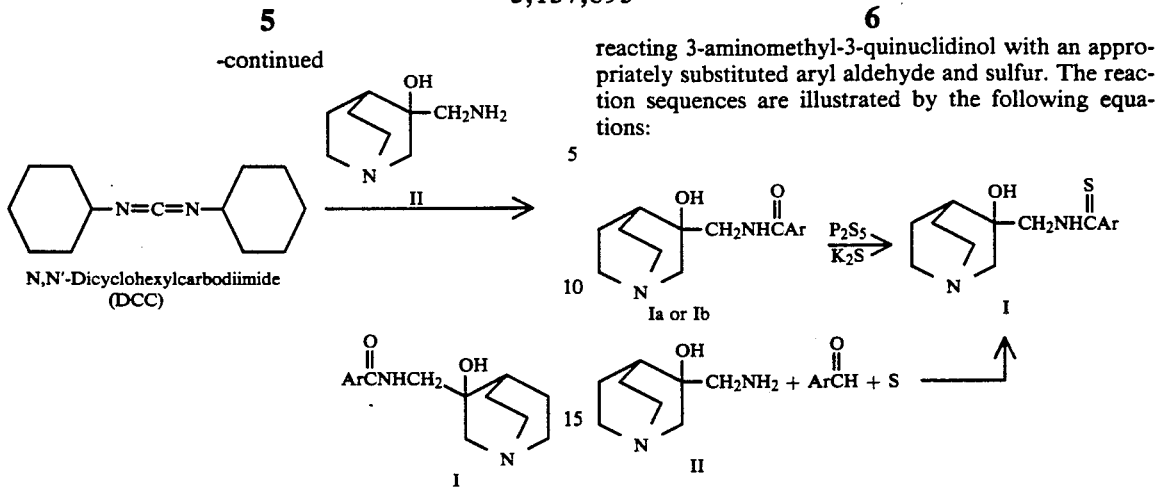

A mixture of an arylcarboxylic acid and 3-aminomethyl-1-azabicyclo[2.2.2]octan-3-ol in an appropriate solvent is treated with N,N'-dicylohexylcarbodiimide to obtain the title compounds.

METHOD D

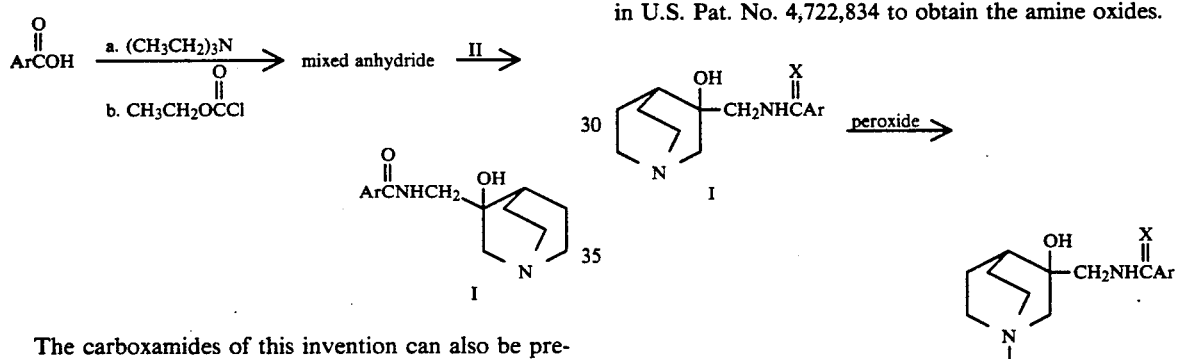

The carboxamides of this invention can also be prepared using the mixed anhydride procedure known to those skilled in the art.

Preparation of 3-(N-thioaroylaminomethyl)-3-quinuclidinols

The preparation of 3-(N-thioaroylaminomethyl)-1-azabicyclo[2.2.2]octan-3-ols of Formula I may be accomplished by mixing and reacting an aroyl compound of Formula 1 with a mixture of potassium sulfide ($K_2S$) and phosphorus pentasulfide ($P_2S_5$) or by mixing and reacting 3-aminomethyl-3-quinuclidinol with an appropriately substituted aryl aldehyde and sulfur. The reaction sequences are illustrated by the following equations:

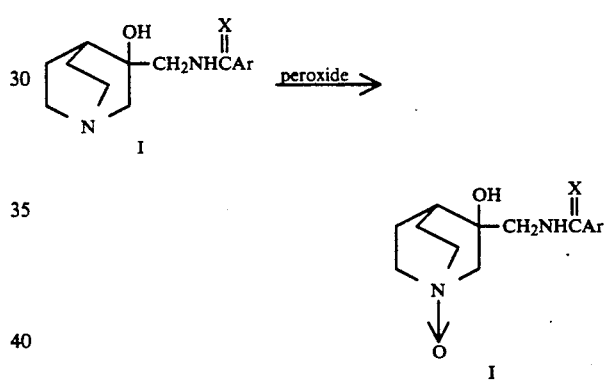

Preparation of 3-[N-aroyl(or thioaroyl-)aminomethyl]-1-azabicyclo[2.2.2]-octan-3-ol-N-oxides The 3-[N-aroyl(or thioaroyl)aminomethyl]-1-azabicyclo[2.2.2]octan-3-ols obtained by the foregoing methods may be oxidized with a peroxide as described in U.S. Pat. No. 4,722,834 to obtain the amine oxides.

Preparation of Intermediates

Precursors (Chemical Intermediates) used in the synthesis of compounds of Formula I are prepared as illustrated by the following equations and laboratory procedures given in the preparations which follow.

Preparation of 2-substituted benzoic acid intermediates (III)

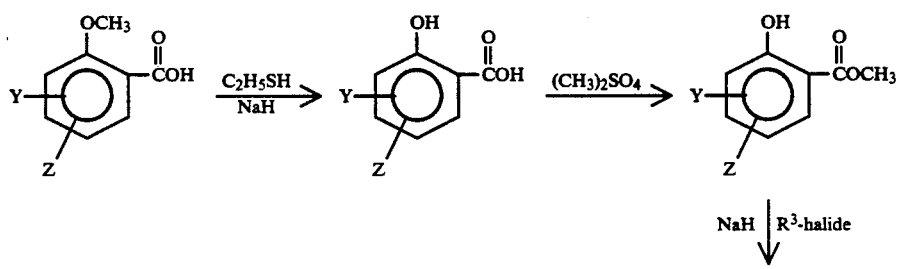

-continued

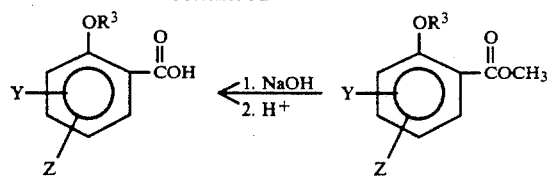

Preparation of 3-aminomethyl-1-azabicyclo[2.2.2]octan-3-ol

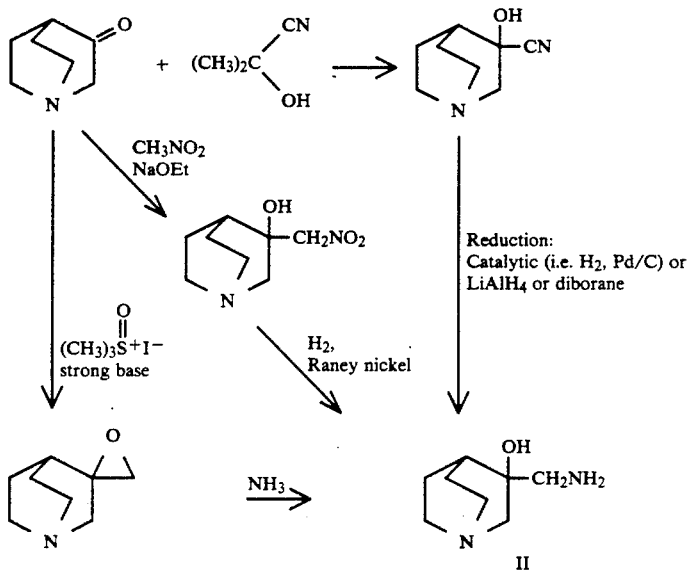

The optical isomers of the invention compounds can be resolved by methods known to those skilled in the art or can be synthesized from the optical isomers of 3-aminomethyl-1-azabicyclo[2.2.2]oct-3-ols.

The foregoing methods of preparation of compounds of Formula I are broadly described and the reactions may not be applicable as described to each compound included within the scope of this invention. Where this occurs can easily be recognized by those skilled in the art and such reaction can be carried out by modifications known to those skilled in the art. Exact conditions may vary with substrates, solvents, temperature, and the like.

Without further elaboration, it is believed that one skilled in the art will be able to carry out the invention. The following preparations and examples are provided merely by way of illustrating the methods of preparation and compounds and are not to be construed as limiting in nature.

PREPARATION 1

3-Nitromethyl-1-azabicyclo[2.2.2]octan-3-ol

A mixture of 3-quinuclidinone (24.4 g, 0.195 mole) and nitromethane (15.9 g, 0.260 mole) in absolute ethanol (100 ml) was added to a cooled (0° C.) mechanically stirred solution of 21% sodium ethoxide/ethanol (64.8 g, 200 mole) in absolute ethanol (300 ml) under nitrogen. The mixture was stirred at room temperature for one hour, then at 55°(±5°) C. for 18 hours. The cooled suspension was treated dropwise with acetic acid (13.2 g, 0.220 mole), filtered through Celite ®, washed with methanol, and concentrated in vacuo. The residue was filtered through alumina (eluted with 1:2 methylene chloride/methanol), concentrated in vacuo, and triturated from acetonitrile to afford 8.44 g (23%) of the title compound as an off-white solid.

PREPARATION 2a 3-(Aminomethyl)-1-azabicyclo[2.2.2]octan-3-ol

A solution of -3-nitromethyl-1-azabicyclo[2.2.2]octan-ol (2.98 g, 0.016 mole) in methanol (150 ml) in a Parr bottle was treated with Raney Nickel (one teaspoon), and subjected to hydrogenation in a Parr apparatus over 2.5 hours. The product solution was filtered through Celite ® and concentrated in vacuo (readily carbonates) to afford 2.36 g (94%) of the title compound as a colorless solid.

PREPARATION 2b 3-(Aminomethyl)-1-azabicyclo[2.2.2]octan-3-ol dihydrochloride

This compound was prepared from 1-azabicyclo[2.2.2]octan-3-methylene oxide according to the procedure given in the U.S. Pat. No. 3,775,419 and isolated in 37% yield as the dihydrochloride salt, mp>300° C. (methanol).

Analysis: Calculated for $C_8H_{16}N_2O \cdot 2HCl$: C, 41.93; H, 7.02; N, 12.22. Found: C, 42.15; H, 8.25; N, 12.11.

PREPARATION 2c 3-(Aminomethyl)-1-azabicyclo[2.2.2]octan-3-ol

A 100 ml 3-neck round bottom flask was charged under nitrogen with 30 ml of a 1.0N lithium aluminum hydride solution in tetrahydrofuran (0.030 mole). The solution was chilled to −20° C. and treated in portions with quinuclidin-3-one cyanohydrin (3.04 g, 0.020 mole). The solution was warmed up to 25° C., stirred for 1 hr, and then heated at reflux temperature for 1 hr. After cooling to 0° C. the mixture was treated cautiously with successive additions of water (1.15 ml), 15% sodium hydroxide solution (1.15 ml), and water (3.5 ml). The solution was filtered and the filtrate concentrated to an oil that was shown by gas chromatography to be a 3:1 mixture of 3-(aminomethyl)-1-azabicyclo[2.2.2]octan-3-ol and 1-azabicyclo[2.2.2]octan-3-ol. This mixture was used without further purification.

PREPARATION 3

3-Hydroxy-1-azabicyclo[2.2.2]octan-3-carbonitrile

The title compound was prepared in 92% yield as a colorless solid, mp 158°–159.5° C. (lit. mp 168°–170° C.) by the procedure of E. E. Mikhlina et al., Khim. Geterotsikl. Soed in Akad. Nauk. Latv. SSR, 1966(2), 243–249 [CA 65:2220a(1966)].

PREPARATION 4

1-Methyl-1H-indazole-3-carboxylic acid

A. Indazole-3-carboxylic acid methyl ester (Intermediate)

A stirred mixture of indazole-3-carboxylic acid (5.00 g, 0.0309 mole), methanesulfonic acid (1 ml), and methanol (100 ml) was heated at reflux temperature for 5 hours and then concentrated to a volume of 30 ml and treated with excess saturated aqueous sodium bicarbonate solution. Water was added to give a volume of 200 ml and the suspended solid was collected by filtration. The wet solid was dissolved in methylene chloride (200 ml), and the solution separated from a small amount of water and some insoluble material. The methylene chloride solution was dried (magnesium sulfate) and concentrated to yield 3.25 g (60%) of indazole-3-carboxylic acid methyl ester.

B. 1-Methyl-1H-indazole-3-carboxylic acid methyl ester (Intermediate)

A solution of indazole-3-carboxylic acid methyl ester (2.76 g, 0.0159 mole) in dry dimethylformamide (20 ml) was added dropwise to a stirred suspension of 60% sodium hydride (oil dispersion) (0.67 g, 0.0176 mole) in dimethylformamide (50 ml). After the addition was completed and the evolution of the hydrogen ceased, the mixture was heated to 80° C. and then cooled to ambient temperature. A solution of methyl iodide (4.23 g, 0.030 mole) in dimethylformamide (10 ml) was added dropwise to the stirred reaction mixture. After stirring for 15 minutes, the mixture was warmed to 50° C. for 30 minutes, and then cooled to ambient temperature. The reaction mixture was diluted to a volume of 300 ml with ice/water and extracted with two 100 ml portions of methylene chloride. The extract was dried (magnesium sulfate), and concentrated to an oil. Dimethylformamide was distilled from the mixture and the residual oil was triturated with petroleum ether to obtain a solid. The solid (1.66 g, 55%) was collected by filtration and recrystallized from isooctane to give 1.20 g; mp 78°–79° C.

C. 1-Methyl-1H-indazole-3-carboxylic acid. (Title compound)

A solution of 1-methylindazole-3-carboxylic acid, methyl ester (1.00 g, 0.0053 mole; was stirred in a mixture of methanol (10 ml)/2N NaOH solution (120 ml) at reflux temperature for 2 hours. After cooling, the mixture was diluted with water (100 ml) and acidified with 6N HCl solution. The white solid that formed was collected by filtration and dried under ambient conditions for 6 days to give 0.86 g (92% yield) of the product; mp 215°–216° C.

Analysis: Calculated for $C_9H_8N_2O_2$: C, 61.36; H, 4.58; N, 15.90. Found: C, 61.25; H, 4.53; N, 15.89.

PREPARATION 5

4-Amino-5-chloro-2-hydroxybenzoic acid

A cooled (5° C.) suspension of 60% sodium hydride/oil dispersion (20.0 g, 0.50 mole) in anhydrous dimethylformamide (300 ml) under nitrogen was treated slowly dropwise with ethyl mercaptan (18.7 g, 0.30 mole) so as to maintain a pot temperature below 15° C., then stirred at room temperature for 15 minutes, cooled (5° C.), and treated in portions with 4-amino-5-chloro-2-methoxybenzoic acid (40.33 g, 0.20 mole). The mixture was heated to 105°±5° C. for 4 hours, cooled, and concentrated in vacuo to remove most of the dimethylformamide, then plunged into water (500 ml). The aqueous solution was extracted with methylene chloride (2×150 ml), and ether (150 ml), acidified with concentrated HCl (55 ml), filtered, and the filter cake washed with water and dried in vacuo to afford 35.7 g of crude product. Crystallization from tetrahydrofuran/hexane afforded 31.3 g (83%) of white solid; mp 192° C.

PREPARATION 6

4-Amino-5-chloro-2-hydroxybenzoic acid, methyl ester

A solution of 4-amino-5-chloro-2-hydroxybenzoic acid (1.88 g, 0.010 mole) in absolute methanol (20 ml) was treated with 25% sodium methoxide/methanol (2.16 g, 0.010 mole), stirred for 30 minutes, and concentrated in vacuo. The solid residue was taken up in anhydrous acetone (30 ml), treated with dimethyl sulfate (1.64 g, 0.013 mole) and refluxed for 2 hours. The resultant solution was diluted with water (100 ml), and the precipitate was filtered, washed with water, and dried exhaustively in vacuo to afford 1.75 g (87%) of the title compound as fine colorless needles. The material was recrystallized from ethyl acetate/hexane; mp 138°–139° C.

Analysis: Calculated for $C_8H_8ClNO_3$: C, 47.66; H, 4.00; N, 6.95. Found: C, 47.60; H, 4.00; N, 6.93.

PREPARATION 7

4-Amino-5-chloro-2-(2-methylthio)ethoxybenzoic acid

A cooled (5° C.) suspension of 60% sodium hydride/oil dispersion (0.52 g, 0.013 mole) in anhydrous dimethylformamide (15 ml) under nitrogen was treated in portions with 4-amino-5-chloro-2-hydroxybenzoic acid methyl ester (0.94 g, 0.005 mole) stirred for 15 minutes at 25° C., treated with (2-chloroethyl)methyl sulfide (1.66 g, 0.015 mole), and heated to 100°±5° C. for 18 hours. The solution was cooled, concentrated in vacuo in order to remove most of the dimethylformamide, and added to water (25 ml). The aqueous solution was extracted with ether (2×25 ml), and the combined extracts were dried (magnesium sulfate), concentrated in vacuo, taken up in 50% aqueous ethanol (50 ml), treated with potassium hydroxide (5.0 g), and refluxed for one hour. The mixture was concentrated in order to remove most of the dimethylformamide, and added to water (25 ml). The aqueous solution was extracted with ether (2×25 ml), and the combined extracts were dried (magnesium sulfate), concentrated in vacuo, taken up in 50% aqueous ethanol (50 ml), treated potassium hydroxide (5.0 g), and refluxed for one hour. The mixture was concentrated in order to remove most of the ethanol, diluted with water to 75 ml total volume, extracted with ether (2×35 ml), and acidified to pH 3 with concentrated HCl. The precipitate was filtered, washed with water, air dried, and recrystallized from ethyl acetate to afford 0.74 g (57%) of the title compound as fine voluminous white needles; mp 137.5°–139.5° C.

Analysis: Calculated for $C_{10}H_{12}ClNO_3S$: C, 45.89; H, 4.62; N,5.35. Found: C, 45.96; H, 4.72; N, 5.32.

PREPARATION 8

4-Amino-5chloro-2-(2-methoxyethoxy)benzoic acid

A suspension of 60% sodium hydride/oil dispersion (1.00 g, 0.025 mole) in anhydrous dimethylformamide (40 ml) under nitrogen was treated with 4-amino-5-chloro-2-hydroxybenzoic acid, methyl ester (4.03 g, 0.020 mole), stirred for 30 minutes, then treated with 2-bromoethyl methyl ether (3.48 g, 0.025 mole). The mixture was heated to 95°±5° C. for 1.5 hours, then cooled and added to water (250 ml). The aqueous suspension was filtered, and the solid was washed with water, air dried, collected, and recrystallized from ether/hexane to afford 2.75 g (53%) of 4-amino-5-chloro-2-(2-methoxyethoxy)benzoic acid methyl ester; mp 121.0°–122.5° C.

A solution of the ester (2.75 g, 0.0106 mole) in 95% ethanol (20 ml) was treated with 50% sodium hydroxide (10 ml) and water (10 ml), and refluxed for one hour. The ethanol was removed in vacuo and replaced with water, and the aqueous solution was extracted with ether (20 ml) and adjusted to pH~4 with concentrated hydrochloric acid (16 ml). A solid soon precipitated, and this was filtered, washed with water, air dried, and recrystallized from ethyl acetate (2 crops) to afford 2.03 g (78%) of the title compound as fine pale tan needles; mp 119°–120° C.

Analysis: Calculated for $C_{10}H_{12}ClNO_4$: C, 48.89; H, 4.92; N, 5.70. Found: C, 48.87; H, 4.94; N, 5.68.

PREPARATION 9

4-Amino-5-chloro-2-[(tetrahydro-2H-pyran-2-yl)methoxy]benzoic acid

A suspension of 50% sodium hydride/oil dispersion (1.00 g, 0.025 mole) in anhydrous dimethylformamide (40 ml) under nitrogen was treated with 4-amino-5-chloro-2-hydroxybenzoic acid methyl ester (4.03 g, 0.020 mole), stirred for 30 minutes, then treated with 2-(bromomethy)tetrahydro-2H-pyran (4.66 g, 0.026 mole). The mixture was heated to 95°±5° C. for 1.5 hours, then cooled and added to water (250 ml). The aqueous mixture was extracted with ether (2×200 ml), and the combined ethereal solution was dried (magnesium sulfate), concentrated in vacuo, an taken up in 95% ethanol (40 ml), water (20 ml) and 50% sodium hydroxide (20 ml) were added, and the mixture was refluxed for one hour, cooled on an ice bath, and concentrated in vacuo in order to remove most of the ethanol. Water was added to a total volume of 200 ml, and the aqueous solution was extracted with ether (2×100 ml), cooled on an ice bath, and adjusted to pH~4 with concentrated hydrochloric acid (32 ml). A solid soon precipitated, and this was filtered, washed with water, air dried, and recrystallized from ethyl acetate to afford 3.45 g (60%) of the title compound as colorless crystals; mp 146.5°–147.5° C.

Analysis: Calculated for $C_{13}H_{16}ClNO_4$: C, 54.65; H, 5.64; N, 4.90. Found: C, 54.68; H, 5.65; N, 4.90.

PREPARATION 10

4-Amino-5-chloro-2-(propenyloxy)benzoic acid

A suspension of 60% sodium hydride/oil dispersion (1.52 g, 0.038 mole) in anhydrous dimethylformamide (50 ml) under nitrogen was treated in portions with 4-amino-5-chloro-2-hydroxybenzoic acid methyl ester (6.05 g, 0.030 mole), stirred at room temperature for 30 minutes, and treated with allyl bromide (4.60 g, 0.038 mole). The mixture was stirred at 95°±5° C. for one hour, cooled to room temperature, and added to water (250 ml). The solid was removed by filtration and saved, and the filtrate was extracted with ether (2×100 ml). The concentrated ethereal extracts were combined with the filtered solid, taken up in 20% aqueous ethanol (100 ml), treated with potassium hydroxide (10 g), and refluxed for 45 minutes. The ethanol was removed in vacuo and the aqueous solution was extracted with ether (50 ml) and petroleum ether (30°–60°, 50 ml), cooled (0° C.), and acidified to pH 4 with concentrated hydrochloric acid (17 ml). The suspension was filtered and solid was air dried, dissolved in methylene chloride (150 ml) containing a little methanol, dried (sodium sulfate), and concentrated in vacuo. Trituration from cold ether/petroleum ethers (30°–60°) and recrystallization from ethyl acetate/hexane (2 crops) afforded 4.25 g (62.2%) of the title compound as a pale tan solid; mp 136°–137° C.

Analysis: Calculated for $C_{10}H_{10}ClNO_3$: C, 52.76; H, 4.43; N, 6.15.Found: C, 52.71; H, 4.42; N, 6.15.

PREPARATION 11

4-Amino-5-chloro-2-[2-(diethylamino)-2-oxoethoxy]-benzoic acid

A cooled (0° C.) suspension of 60% sodium hydride/oil dispersion (1.40 g, 0.035 mole) in anhydrous dimethylformamide (60 ml) under nitrogen was treated in portions with 4-amino-5-chloro-2-hydroxybenzoic acid methyl ester (6.05 g, 0.030 mole) and stirred for 30 minutes at room temperature. 2-Chloro-N,N-diethylacetamide (5.40 g, 0.036 mole) was added, and the mixture was stirred at 100°–110° C. for 3 hours until gas chromatography indicated absence of 4-amino-5-chloro-2-hydroxybenzoic acid methyl ester. The solution was cooled and added to ice water (350 ml), then extracted with ether (3×200 ml). The combined organic solution was dried (magnesium sulfate) and concentrated in vacuo. Filtration through alumina (eluted with 3% methanol/methylene chloride) and trituration from petroleum ethers (30°–60°) afforded 8.66 g (92%) of 4-amino-5-chloro-2-[2-(diethylamino)-2-oxoethoxy]-benzoic acid methyl ester as a colorless solid; mp 97.5°–99.5° C. (ethyl acetate/hexane).

A solution of the ester (7.87 g, 25 mole) in water (70 g) containing methanol (40 g) was treated with 50% sodium hydroxide (10 g) and heated to 60° C. for 30 minutes. The mixture was neutralized with 3N HCl solution until a precipitate formed (pH~3). The solid was filtered, washed with water, air dried, and recrystallized from 2-propanol to afford (2 crops) 5.12 g (68%) of the title compound as fine colorless needles; mp 186.5°–188.0° C.

Analysis: Calculated for $C_{13}H_{17}ClN_2O_4$: C, 51.92; H, 5.70; N, 9.31. Found: C, 52.02; H, 5.78; N, 9.32.

PREPARATION 12

5-Chloro-2-methoxy-4-[(methylsufonyl)amino]benzoic acid

A cooled (−60° C.) solution of diisopropylamine (11.13 g, 0.110 mole) in anhydrous tetrahydrofuran (150 ml) under nitrogen was treated (via syringe) with 2.4N n-butyllithium/hexane (0.105 mole), warmed to −20° C., stirred for 5 minutes, then treated in portions with 4-(N-acetylamino)-5-chloro-2-methoxybenzoic acid, methyl ester (25.8 g, 0.100 mole). After 30 minutes at 25° C., the mixture was cooled (0° C.), treated dropwise with a solution of methanesulfonyl chloride (25.0 g, 0.218 mole) in anhydrous tetrahydrofuran (50 ml), and maintained at room temperature for 30 minutes and at 50° C. for one hour. The mixture was partially concentrated in vacuo and added to ice water (600 ml), and the aqueous mixture was extracted with methylene chloride (3×250 ml). The combined organic solution was dried (sodium sulfate), concentrated in vacuo, taken up in 60:40 water/ethanol (300 ml), treated with potassium hydroxide (33.6 g, 0.60 mole), and refluxed for three hours. Most of the ethanol was removed in vacuo and replaced with water, and the aqueous solution was extracted with ether (2×200 ml), then cooled in an ice bath and treated with concentrated hydrochloric acid solution (60 ml). The suspension was filtered and the solid was washed with water, air dried, and recrystallized from 95% ethanol to afford 14.60 g (52%) of the title compound as a colorless solid; mp 248°-250° C.

Analysis: Calculated for $C_9H_{10}ClNO_5S$: C, 38.65; H, 3.60; N, 5.01. Found: C, 38.81; H, 3.52; N, 4.93.

PREPARATION 13

5-Chloro-2-methoxy-4-(methylamino)benzoic acid

The title compound was prepared by the procedure published in J.Med.Chem. 1981, 24(10), 1224–1230.

PREPARATION 14

4-Amino-5-chloro-2-[(3-iodophenyl)methoxy]benzoic acid

A cooled (0° C.) suspension of 60% sodium hydride/oil dispersion (1.32 g, 33 mmol) in anhydrous N,N-dimethylformamide (45 mL) under nitrogen was carefully treated in portions with 4-amino-5-chloro-2-hydroxybenzoic acid, methyl ester (6.05 g, 30 mmol), maintained at 40°-45° C. for 1 hr, then treated with 3-iodobenzyl bromide (10.7 g, 36 mmol) and heated to 100°±5° C. for 1 hr. The solution was cooled and added to ice water (250 mL), and after a few minutes a precipitate formed which was collected by filtration. The solid was washed with water, air dried, and taken up in methylene chloride and filtered through alumina (eluted with 5% methanol/methylene chloride). The filtrate was concentrated in vacuo and the residue was triturated from petroleum ethers (30°-60° C.). The solid was taken up in 50% aqueous methanol (200 mL), treated with 50% sodium hydroxide (22 g), refluxed for 3 hr, and concentrated in vacuo to remove most of the methanol. The resultant suspension was cooled on an ice bath, treated with concentrated hydrochloric acid to pH 3 (about 30 mL), then filtered. The solid was washed with water, air dried overnight, and triturated from acetonitrile to afford 8.10 g (67%) of pale orange solid; mp (EtOH/MeOH) 172°-173° C.

Analysis: Calculated for $C_{14}H_{11}ClINO_3$: C, 41.66; H, 2.75; N, 3.47. Found: C, 41.67; H, 2.71; N, 3.46.

EXAMPLE 1

5-Chloro-N-(3-hydroxy-1-azabicyclo[2.2.2]oct-3-ylmethyl)-2-methoxy-4-(methylamino)benzamide A solution of 5-chloro-2-methoxy-4-(methylamino)-benzoic acid (3.02 g, 0.014 mole) in anhydrous tetrahydrofuran (15 ml) under nitrogen was treated with 1,1'-carbonyldiimidazole (2.35 g, 0.0145 mole) and stirred for one hour. A solution/suspension of 3-aminomethyl-1-azabicyclo[2.2.2]octan-3-ol (2.34 g, 15 mole) in tetrahydrofuran (15 ml) containing a little N,N-dimethylformamide for solubility was added slowly over a few minutes, and the mixture was stirred overnight (18 hours) at room temperature and for one hour at 60° C., then concentrated in vacuo. The white solid was partitioned between 1.0N sodium carbonate (100 ml) and methylene chloride (200 ml) containing a little methanol, and the organic layer was separated. The aqueous solution was extracted with methylene chloride (2×50 ml) containing a little methanol, and the combined organic solution was dried (sodium sulfate) and passed through a short column of alumina (eluted with 10% methanol/methylene chloride). The filtrate was concentrated in vacuo, triturated from ether, and triturated from acetonitrile to afford 2.67 g (54%) of the title compound as a colorless solid; mp 236°-237° C. (dec).

Analysis: Calculated for $C_{17}H_{24}ClN_3O_3$: C, 57.70; H, 6.84; N, 11.88. Found: C, 57.45; H, 6.88; N, 11.86.

EXAMPLE 2

4-Amino-5-chloro-N-(3-hydroxy-1-azabicyclo[2.2.2]oct-3-ylmethyl)-2-methoxybenzamide, monohydrochloride, hemihydrate A suspension of 4-amino-5-chloro-2-methoxybenzoic acid (4.03 g, 0.020 mole) in anhydrous tetrahydrofuran (20 ml) under nitrogen was treated with 1,1'-carbonyldiimidazole (3.33 g, 0.0205 mole), stirred at room temperature for one hour, then added to a cooled (0° C.) solution/suspension of 3-aminomethyl-1-azabicyclo[2.2.2]octan-3-ol in anhydrous tetrahydrofuran (20 ml). The mixture was stirred at room temperature for 18 hours, then at 60° C. for one hour, and concentrated in vacuo. The residue was partitioned between methylene chloride (200 ml) containing a little 2-propanol and 1.0N sodium carbonate (100 ml). The combined organic solution was dried (sodium sulfate), concentrated in vacuo, taken up in methylene chloride containing a little methanol, and filtered through alumina (eluted with 15% methanol/methylene chloride). The filtrate was concentrated in vacuo and the solid residue was triturated from cold acetone and recrystallized from acetonitrile containing a little methanol (2 crops), then recrystallized again from acetonitrile to afford 3.01 g (44%) of the free base of the title compound as colorless crystals. A suspension of the amide (2.22 g, 0.00853 mole) in absolute tetrahydrofuran (50 ml) was partially solubilized with a little methanol, then treated with excess ethereal hydrogen chloride. The resultant precipitate was filtered under nitrogen, washed with tetrahydrofuran, dried in vacuo, and triturated from acetonitrile to afford 2.20 g (87%) of the title compound as a colorless solid; mp 160°-162° C.

Analysis: Calc. for $C_{16}H_{22}ClN_3O_3\cdot HCl\cdot\frac{1}{2}H_2O$: C, 49.88; H, 6.28; N, 10.91. Found: C, 50.20; H, 6.29; N, 11.04.

EXAMPLE 3

N-(3-Hydroxy-1-azabicyclo[2.2.2]oct-3-ylmethyl)-1H-indole-3-carboxamide fumarate hydrate (2:4:1)

A suspension of indole-3-carboxylic acid (1.94 g, 0.012 mole) in anhydrous 2:1 dimethylformamide/tetrahydrofuran (15 ml) under nitrogen was treated with 1,1'-carbonyldiimidazole (2.27 g, 0.014 mole), stirred for two hours, and degassed over 15 minutes with a stream of nitrogen. A solution containing 3-aminomethyl-1-azabicyclo[2.2.2]octan-3-ol in tetrahydrofuran (10 ml) was added and the mixture stirred for 18 hours at 25° C. and for four hours at 50° C., then concentrated in vacuo. The residue was partitioned between saturated sodium carbonate (75 ml) and toluene (150 ml) containing some 2-propanol, and the organic layer was separated. The aqueous solution was extracted with toluene (75 ml) containing some 2-propanol, and the combined organic solution was dried (sodium sulfate), and concentrated in vacuo. The gummy residue was washed with water, redissolved in toluene containing some 2-propanol, dried (sodium sulfate), concentrated in vacuo, and taken up in methanol (20 ml). A warm solution of fumaric acid (2.0 g, 0.0172 mole) in methanol (30 ml) was added, and after 15 minutes the solution was concentrated in vacuo to a gummy oil. This was triturated successively from ether, acetonitrile, and ethyl acetate to afford (after drying) 3.36 g (52%) of the title compound as a colorless solid.

Analysis: Calc'd for $C_{17}H_{21}N_3O_2\cdot 2(C_4H_4O_4)\cdot\frac{1}{2}H_2O$: C, 55.55; H, 5.59; N, 7.77. Found: C, 55.18; H, 5.49; N, 7.63.

EXAMPLE 4

4-Amino-5-chloro-2-hydroxy-N-(3-hydroxy-1-azabicyclo[2.2.2]oct-3-ylmethyl)benzamide A solution of 4-amino-5-chloro-2-hydroxybenzoic acid (1.88 g, 10 mmol) in anhydrous tetrahydrofuran (10 ml) under nitrogen was treated with 1,1'-carbonyldiimidazole (1.87 g, 11.5 mmol), stirred for one hour at room temperature, and degassed over 15 minutes under a stream of nitrogen. A solution of the mixture containing 3-aminomethyl-1-azabicyclo[2.2.2]octan-3-ol in anhydrous tetrahydrofuran (10 ml) was added, and the mixture was stirred for 18 hours at room temperature and for two hours at 50° C. The suspension was filtered and the solid washed with tetrahydrofuran, collected, and recrystallized from acetonitrile containing a little methanol, then from ethanol to afford 1.82 g (56%) as a colorless solid; mp 259° C. (dec.).

Analysis: Calculated for $C_{15}H_{20}ClN_3O_3$: C, 55.30; H, 6.19; N, 12.90. Found: C, 55.20; H, 6.24; N, 12.84.

EXAMPLE 5

4-Amino-5-chloro-N-(3-hydroxy-1-azabicyclo[2.2.2]oct-3-ylmethyl)-2-(2-methoxyethoxy)benzamide fumarate hydrate (2:2:1)

A solution of 4-amino-5-chloro-2-(2-methoxyethoxy)benzoic acid in anhydrous tetrahydrofuran (12 ml) under nitrogen was treated with 1,1'-carbonyldiimidazole (1.87 g, 0.0115 mole), stirred for one hour, and degassed over 15 minutes with a stream of nitrogen. A solution of the mixture containing 3-aminomethyl-1-azabicyclo[2.2.2]octan-3-ol prepared from in anhydrous tetrahydrofuran (10 ml) was added, and the mixture was stirred for 18 hours at room temperature and for one hour at 50° C., then concentrated in vacuo. The residue was partitioned between saturated sodium carbonate (75 ml) and toluene (150 ml) containing some 2-propanol, and the organic layer was separated. The aqueous solution was extracted with toluene (2×50 ml) containing some 2-propanol, and the combined organic solution was dried (sodium sulfate) and concentrated in vacuo. Alumina chromatography (eluted with 2% methanol/tetrahydrofuran, then with 25% methanol/tetrahydrofuran) afforded 2.09 g (54%) of the free base. A solution of the free base (1.88 g, 0.0049 mole) in methanol (15 ml) was treated with a warm solution of fumaric acid (1.16 g, 0.010 mole) in methanol (20 ml). After a while a precipitate formed and the suspension was diluted with ether (65 ml) and filtered. The solid was washed with ether, collected, and dried in vacuo at 80° C. to afford the title compound as a colorless solid; mp 134.0°–135.5° C.

Analysis: Calc'd. for $C_{18}H_{26}ClN_3O_4\cdot C_4H_4O_4\cdot\frac{1}{2}H_2O$: C, 51.92; H, 6.14; N, 8.26. Found: C, 51.70; H, 5.96; N, 8.19.

EXAMPLE 6

5-Chloro-N-(3-hydroxy-1-azabicyclo[2.2.2]oct-3-ylmethyl)-2-methoxy-4-[(methylsulfonyl)amino]benzamide fumarate (1:1)

A suspension of 5-chloro-4-methanesulfonylamino-2-methoxybenzoic acid (2.80 g, 0.010 mole) in anhydrous tetrahydrofuran (10 ml) and dimethylformamide (3 ml) under nitrogen was treated with 1,1'-carbonyldiimidazole (1.87 g, 0.0115 mole), stirred for two hours at room temperature (solution cleared), and degassed over 15 minutes with a stream of nitrogen. A solution of the mixture containing 3-aminomethyl-1-azabicyclo[2.2.2]-octan-3-ol in anhydrous tetrahydrofuran (10 ml) was added, and the mixture was stirred overnight (18 hours), then for four hours at 50° C. The suspension was filtered and the solid washed with tetrahydrofuran and recrystallized from acetonitrile containing a little methanol to afford 2.79 g (67%) of a colorless solid; mp 193.5°–194.5° C. A suspension of a portion of the solid (2.43 g, 0.0058 mole) in methanol (40 ml) was treated with fumaric acid (1.05 g, 0.009 mole). After a few minutes the suspension cleared, and this was warmed and filtered. The filtrate was diluted with ether (40 ml), and a solid soon crystallized. This was filtered, washed with ether, collected, and dried in vacuo at 110° C. to afford 2.86 g (92%) of the title compound as colorless crystals; mp 215°–216° C.

Analysis: Calculated for $C_{17}H_{24}ClN_3O_5S\cdot C_4H_4O_4$: C, 47.24; H, 5.29; N, 7.87. Found: C, 47.20; H, 5.32; N, 7.85.

EXAMPLE 7

N-(3-Hydroxy-1-azabicyclo[2.2.2]octan-3-ylmethyl)-1-methylindole-3-carboxamide fumarate (1:1)

A solution of 1-methylindole-3-carboxylic acid (1.58 g, 0.009 mole) in anhydrous tetrahydrofuran (5 ml) under nitrogen was treated with 1,1'-carbonyldiimidazole (1.62 g, 0.010 mole), and after a few minutes the bubbling stopped and a precipitate formed. This was diluted with anhydrous N,N-dimethylformamide (5 ml), stirred for one hour, and degassed for 15 minutes under a stream of nitrogen. A solution containing 3-aminomethyl-1-azabicyclo[2.2.2]octan-3-ol in 1:1 tetrahydrofuran-dimethylformamide (10 ml) was added and the mixture stirred for 20 hours at room temperature and for two hours 50° C., then concentrated in vacuo. The residue was partitioned between 1.0N sodium carbonate (75 ml) and toluene (100 ml) containing some 2-propanol, and the organic layer was separated. The aqueous solution was extracted with toluene (2×50 ml) containing some 2-propanol, and the combined organic solution was dried (sodium sulfate) and concentrated in vacuo. The residue was washed with water and dried azetropically with toluene to afford 1.74 g (62%) of the free base as a colorless gum.

A solution of the free base (1.66 g, 0.0053 mole) in methanol (15 ml) was treated with fumaric acid (1.05 g, 0.009 mole) and warmed until all fumaric acid dissolved. The mixture was cooled, diluted with ether (30 ml), and a solid soon precipitated. This was cooled (0° C.) stirred for an hour, filtered, and the solid washed with ether, collected, and recrystallized from methanol (2 crops) to afford 1.60 g (70%) of the title compound as a colorless solid; mp 213.0°–214.5° C. (foams).

Analysis: Calculated for $C_{18}H_{23}N_3O_2 \cdot C_4H_4O_4$: C, 61.53; H, 6.34; N, 9.78. Found: C, 61.34; H, 6.40; N, 9.58.

EXAMPLE 8

N-(3-Hydroxy-1-azabicyclo[2.2.2]oct-3-ylmethyl)-1-methyl-1H-indazole-3-carboxamide A suspension of 1-methyl-1H-indazole-3-carboxylic acid (1.76 g, 0.0101 mole) in anhydrous tetrahydrofuran (6 ml) under nitrogen was treated with 1,1'-carbonyldiimidazole (1.87 g, 0.0115 mole). After a few minutes bubbling commenced and the solid dissolved, and, after a few more minutes, a precipitate formed. The suspension was diluted with anhydrous N,N-dimethylformamide (3 ml), stirred for two hours, then degassed over 15 minutes under a stream of nitrogen. A solution of the free base of 3-aminomethyl-1-azabicyclo[2.2.2]octan-3-ol (2.03 g, 0.013 mole) in anhydrous tetrahydrofuran (6 ml) was added, and the mixture was stirred at room temperature for 18 hr and at 50° C. for 4 hr, then concentrated in vacuo. The residue was partitioned between 1.0N sodium carbonate (50 ml) and toluene (75 ml) containing some 2-propanol. The organic layer was separated and the aqueous solution was extracted with toluene (2×30 ml) containing some 2-propanol). The combined organic solution was concentrated in vacuo, and the residual gum washed with water (50 ml) to remove most of the imidazole and then dried azeotropically with toluene. The gum was taken up in tetrahydrofuran and filtered through alumina (eluted with 20% methanol/tetrahydrofuran) and the concentrated filtrate was recrystallized from acetonitrile to afford 1.23 g (39%) of the title compound as a pale yellow solid; mp 147°–149° C.

Analysis: Calculated for $C_{17}H_{22}N_4O_2$: C, 64.95; H, 7.05; N, 17.82. Found: C, 64.78; H, 7.06; N, 17.82.

EXAMPLE 9

2-Amino-N-(3-hydroxy-1-azabicyclo[2.2.2]oct-3-ylmethyl)-6-methoxy-5-pyrimidinecarboxamide Using the method of Example 2 where 2-amino-4-methoxypyrimidine-5-carboxylic acid (Ger. Offen. 2,906,461) is substituted for 4-amino-5-chloro-2-methoxybenzamide, the title compound is obtained.

EXAMPLE 10

N-(3-hydroxy-1-azabicyclo[2.2.2]oct-3-ylmethyl)-1H-indazole-3-carboxamide

Using the method of Example 2 where indazole-3-carboxylic acid is substituted for 4-amino-5-chloro-2-methoxybenzoic acid, the title compound is obtained.

EXAMPLE 11

4-Amino-5-chloro-N-(3-hydroxy-1-azabicyclo[2.2.2]oct-3-ylmethyl)-2-[2-methylthio)ethoxy]benzamide Using the procedure of Example 2, where 4-amino-5-chloro-2-[2-methylthio)]ethoxybenzoic acid is substituted for 4-amino-5-chloro-2-methoxybenzoic acid, the title compound is obtained.

EXAMPLE 12

4-Amino-5-chloro-N-(3-hydroxy-1-azabicyclo[2.2.2]oct-3-ylmethyl)-2-[(tetrahydro-2H-pyran-2-yl)methoxy]benzamide Using the procedure of Example 2 where 4-amino-5-chloro-2-[(tetrahydro-2H-pyran-2-yl)methoxy]benzoic acid is substituted for 4-amino-5-chloro-2-methoxybenzoic acid, the title compound is obtained.

EXAMPLE 13

4-Amino-5-chloro-N-(3-hydroxy-1-azabicyclo[2.2.2]oct-3-ylmethyl)-2-(2-propenyloxy)benzamide Using the procedure of Example 2 where 4-amino-5-chloro-2-(2-propenyloxy)benzoic acid is substituted for 4-amino-5-chloro-2-methoxybenzoic acid, the title compound is obtained.

EXAMPLE 14

4-Amino-5-chloro-2-[2-(diethylamino)-2-oxoethoxy]-N-(3-hydroxy-1-azabicyclo[2.2.2]oct-3-ylmethyl)benzamide Using the procedure of Example 2 where 4-amino-5-chloro-2-[2-(diethylamino)-2-oxoethoxy]benzoic acid is substituted for 4-amino-5-chloro-2-methoxybenzoic acid, the title compound is obtained.

EXAMPLE 15

4-(Acetylamino)-N-(3-hydroxy-1-azabicyclo[2.2.2]octan-3-ylmethyl)benzamide

Using the procedure of Example 2 where 4-acetamidobenzoic acid is substituted for 4-amino-5-chloro-2-methoxybenzoic acid, the title compound is obtained.

EXAMPLE 16

4-Amino-N-(3-hydroxy-1-azabicyclo[2.2.2]octan-3-ylmethyl)benzamide

Using the procedure of Example 2 where 4-aminobenzoic acid is substituted for 4-amino-5-chloro-2-methoxybenzoic acid, the title compound is obtained.

EXAMPLE 17

3-Iodo-N-(3-hydroxy-1-azabicyclo[2.2.2]octan-3-ylmethyl)benzamide

Using the procedure of Example 2 where 3-iodobenzoic acid is substituted for 4-amino-5-chloro-2-methoxybenzoic acid, the title compound is obtained.

EXAMPLE 18

N-(3-Hydroxy-1-azabicyclo[2.2.2]octan-3-ylmethyl)-4-methoxy-2-(methylamino)pyrimidine-5-carboxamide Using the procedure of Example 2 where 4-methoxy-2-(methylamino)pyrimidine-5-carboxamide is substituted for 4-amino-5-chloro-2-methoxybenzoic acid, the title compound is obtained.

EXAMPLE 19

4-Amino-5-chloro-N-(3-hydroxy-1-azabicyclo[2.2.2]oct-3-ylmethyl)-2-[2-(methylsulfinyl)ethoxy]benzamide 4-Amino-5-chloro-N-(3-hydroxy-1-azabicyclo[2.2.2]octan-3-ylmethyl)-2-[2-(methylthio)ethoxy]benzamide is oxidized by methods known to those skilled in the art to obtain the title compound.

EXAMPLE 20

4-Amino-5-chloro-N-(3-hydroxy-1-azabicyclo[2.2.2]octan-3-ylmethyl)-2-methoxythiobenzamide 4-Amino-5-chloro-N-(3-hydroxy-1-azabicyclo[2.2.2]octan-3-ylmethyl)2-methoxybenzamide is reacted with phosphorus pentasulfide and potassium sulfide using methods known to those skilled in the art to obtain the title compound.

EXAMPLE 21

4-Amino-5-chloro-N-(3-hydroxy-1-azabicyclo[2.2.2]oct-3-ylmethyl)-2-methoxybenzamide N-oxide hydrochloride This amine oxide is obtained by oxidation of 4-amino-5-chloro-N-(3-hydroxy-1-azabicyclo[2.2.2]oct-3-ylmethyl)-2-methoxybenzamide using procedures disclosed in U.S. Pat. No. 4,722,834.

EXAMPLE 22

N-(3-Hydroxy-1-azabicyclo[2.2.2]oct-3-ylmethyl)-4-[(methylsulfonyl)amino]-benzamide hemihydrate A solution/suspension of 4-[(methanesufonyl)amino]-benzoic acid (1.62 g, 7.5 mmol) in anhydrous tetrahydrofuran (6 ml) under nitrogen was treated with 1,1'-carbonyldiimidazole (1.38 g, 8.5 mmol), stirred for 45 minutes, and degassed under a stream of nitrogen over 15 minutes. A solution of 3-hydroxy-1-azabicyclo[2.2.2]oct-3-ylmethanamine (1.56 g, 10 mmol) in anhydrous tetrahydrofuran (6 mL) was added, and the mixture soon became cloudy. After 18 hours at room temperature and 90 minutes at 50° C. the mixture was concentrated in vacuo and the residue was triturated from acetonitrile. The foamy solid thus obtained was filtered through alumina (eluted with 1:1 methanol/tetrahydrofuran) and the filtrate was concentrated in vacuo and recrystallized from 2-propanol/ether to afford 1.92 g (71%) of the title compound as a hygroscopic voluminous colorless solid (water soluble); mp 123°–125° C. (foam).

Analysis: Calculated for $C_{16}H_{23}N_3O_4S \cdot \frac{1}{2}H_2O$: C, 53.02; H, 6.67; N, 11.59. Found: C, 53.27; H, 6.86; N, 11.65.

EXAMPLE 23

4-Amino-5-chloro-N-(3-hydroxy-1-azabicyclo[2.2.2]oct-3-ylmethyl)-2-[(3-iodophenyl)methoxy]benzamide Following the procedure of Example 2, the title compound is prepared from 3-hydroxy-1-azabicyclo[2.2.2]oct-3-ylmethanamine and 4-amino-5-chloro-2-[(3-iodophenyl)methoxy]benzamide.

TABLE 1

$$\underset{\text{ArCNHCH}_2}{\overset{X}{\underset{\|}{\text{Ar}}}}\text{—}\underset{N}{\overset{OH}{\bigtriangleup}}$$

| Example | Ar | X | Salt |
|---|---|---|---|
| 1. | 2-CH₃O-4-CH₃NH-5-ClC₆H₂— | O | — |
| 2. | 2-CH₃O-4-NH₂-5-ClC₆H₂— | O | HCl.0.5H₂O |
| 3. | 3-Indolyl | O | Fumarate.0.5H₂O |
| 4. | 2-OH-4-NH₂-5-ClC₆H₂ | O | — |
| 5. | 2-CH₃OCH₂CH₂O-4-NH₂-5-ClC₆H₂ | O | Fumarate.0.5H₂O |
| 6. | 2-CH₃O-4-CH₃SO₂NH-5-ClC₆H₂ | O | Fumarate.0.5H₂O |
| 7. | 1-CH₃-indol-3-yl- | O | Fumarate |
| 8. | 1-Methylindazol-3-yl | O | — |
| 9. | H₂N-(pyrimidinyl)-OCH₃ | O | — |
| 10. | 1H-Indazol-3-yl | O | — |
| 11. | 2-CH₃SCH₂CH₂O-4-NH₂-5-ClC₆H₂ | O | — |
| 12. | (tetrahydropyranyl-CH₂O)-(H₂N)-(Cl)-C₆H₂ | O | — |
| 13. | 4-NH₂-5-Cl-2-(CH₂=CHCH₂O)C₆H₂— | O | — |
| 14. | (C₂H₅)₂NCCH₂O-(H₂N)-(Cl)-C₆H₃ | O | — |
| 15. | 4-CH₃C(O)NHC₆H₄— | O | — |
| 16. | 4-NH₂C₆H₄— | O | — |
| 17. | 3-IC₆H₄— | O | — |
| 18. | CH₃NH-(pyrimidinyl)-OCH₃ | O | — |

TABLE 1-continued

ArCNHCH₂ structure with X=O/S, OH, and bicyclic amine N group

| Example | Ar | X | Salt |
|---|---|---|---|
| 19. | (3-methylsulfinyl-ethoxy)-4-chloro-aniline structure | O | — |
| 20. | 4-methoxy-2-chloro-aniline (CH₃O, H₂N, Cl) structure | S | — |
| 21. | 2-CH₃O-4-NH₂-5-ClC₆H₂ | O | N-oxide-HCl |
| 22. | 4-CH₃SO₂NHC₆H₄ | O | 0.5H₂O |
| 23. | 4-NH₂-5-Cl-2-(3-IC₆H₄CH₂O)C₆H₂— | N | — |

PHARMACOLOGICAL METHODS

A. Gastric Emptying Activity

The procedure used to test compounds of the present invention for gastric motility enhancing activity was that of Droppleman et al., J. Pharmacol. Methods, 4, 227(1980).

Each animal was dosed intraperitoneally (9.0 mg/kg) with a test compound or control. After 30 minutes each animal was given 3 ml of a methylcellulose-based test meal formulation. Sixty minutes after administration of the test meal, each animal was killed by cervical dislocation, and the stomach was removed and weighed. The stomach was cut open, rinsed and dried, and reweighed. The difference between the full and empty weights (amount of meal remaining in stomach) was subtracted from the original test meal weight to determine the meal amount emptied from the stomach during the test period.

| Example | Gastric Emptying % Increase | Dose mg/kg IP |
|---|---|---|
| 1 | 41 | 9 |
| 2 | 41 | 9 |
| 4 | 35 | 10 |
| 5 | 36 | 10 |
| 7 | 31 | 10 |

B. Antiemetic Activity

The action of compounds of this invention in controlling emesis caused by administration of platinum-based anticancer drugs is demonstrated by the following procedure which is a modification of the method of Gylys, et al., Res. Comm. Chem. Path. Pharm. 23(1), 61–68 (1979):

Adult, mongrel, unfasted dogs of both sexes were randomly assigned into treatment groups, with each treatment group consisting of four dogs. On the dosing day all dogs were given cisplatin, 3.0 mg/kg, intravenously. Sixty minutes later, the dogs in the control treatment group were given deionized water 0.1 ml/kg intravenously, the dogs in the test group were given the test compound at an appropriate dose intravenously. All doses were administered as a solution by means of a syringe and needle, and each dog's emetic episodes were recorded for 5 hr after the administration of cisplatin.

| Example | Dose mg/kg IP | Emesis % Decrease |
|---|---|---|
| 1 | 1.0 | −58 |
| 2 | 3.16 | −88 |
| 3 | 3.16 | −92 |
| 5 | 3.16 | −85 |
| 6 | 1.0 | −52 |
| 8 | 1.0 | −62 |

When the following anticancer drugs, mechlorethamine hydrochloride, doxorubicin, dactinomycin, or dacarbazine are substituted for cisplatin in the foregoing test procedure, efficacy in controlling emesis with compounds of Formula I is expectable and is intended to be indicative of the general utility of the compounds in controlling emesis caused by non-platinum based anticancer drugs. Examples of additional non-platinum drugs for which Formula I compounds are anticipated to be effective are: cytoxin, leurocristine, procarbazine, methotrexate and fluorouracil.

Compounds of Formula I are also expected to be effective in reducing emesis caused by radiation.

C. Anxiolytic Activity

Anxiolytic properties of test compounds in mice are determined by the method described by Young and Johnson, Soc. Neurosci. Abs. 1988, 14, 207 and is a modification of the procedure described by Costall and Naylor, Brit. J. Pharmacol. 1988, 93, 985–993. A two-compartment light-dark activity monitoring device (Digiscan Model RXYZCM 16, Omnitech Electronics Inc., Columbus, Ohio) was used. A 90 W light source located 30 cm above the box provided light to the lit portion of the apparatus. Behavioral testing was conducted in a sound-attenuated, darkened room illuminated with red light (25 W red bulb) only.

Each animal (mouse) received a dose or doses of either the test, reference, or control article. The animal was placed at the center of the illuminated area and the behavioral activity tallied over a 5 min period by use of the Digiscan analyzer. Behavioral variables recorded included: the time spent in the lit and dark areas, the number of rearings in the lit and dark areas, the number of locomotor activity counts in the lit and dark areas, the number of transitions between the lit and dark or dark and lit areas, the latency to make the first transition from the lit area to the dark area, rearing time in the lit and dark areas, locomotor time in the lit and dark areas, and resting time in the lit and dark areas. Appropriate statistical analyses for each measure were performed. Significant increases in one or more of the parameters associated with behavior of the animals in the lit area versus behavior in the dark area correspond to active, non sedating anxiolytic compounds. The compound of Example 2 increased the amount of time spent in the lit area by 52% at 0.1 mg/kg (IP).

D. Serotonin Antagonism

Test compounds were evaluated for antagonism of serotonin induced bradycardia in rats (vonBezold-Jarisch reflex) based on the procedure of Richardson et al. Nature (1985), 316, 126–131. Male Sprague-Dawley rats are anesthesized with urethane and a pressure transducer connected to the carotid artery via a cannula for monitoring the heart rate and blood pressure. Serotonin (10 μg/kg) is given intravenously into the jugular vein, causing bradycardia. After 5 minutes the test compound is administered intravenously and the reduction of bradycardia determined. Only those rats in which the heart rate is reduced by 50% after administration of serotonin are used. Significant differences are determined according to standard statistical methods. With the compound of Example 2, a 31% decrease in bradycardia (0.03 mg/kgIV) was observed and with the compound of Example 7, a 82% decrease in bradycardia (0.03 mg/kgIV) was observed.

PHARMACEUTICAL METHODS AND COMPOSITIONS

Generally, the method of controlling emesis, gastric emptying, arrhythmia, anxiety and undesirable effects of serotonin in accordance with this invention comprises administering to warm blooded animals including human beings a 3-[N-aroyl(or thioaroyl)aminomethyl]-1-azabicyclo[2.2.2]octan-3-ol of Formula I, or a non-toxic organic or inorganic acid addition salt thereof in a wide variety of pharmaceutical forms well known in the art, preferably with a non-toxic pharmaceutical carrier such as is described below in an amount to control emesis and/or facilitate gastric emptying and/or decrease anxiety and/or selectively inhibit or modulate the effects of serotonin and/or correct cardiac arrhythmias. The active agent is administered orally, subcutaneously, intravenously or intramuscularly or parenterally and, if necessary, in repeated doses until satisfactory response is obtained. Coformulation and/or co-administration of the compounds of Formula I and the anticancer drug is within the purview of the method of this invention.

In the particular method of controlling emesis due to administration of anticancer drugs in cancer treatment, it may at times be desirable to administer a mixture comprised of compounds of Formula I, and the anticancer drug to the animal, including humans, the daily dosage being within the range cited above below.

The pharmaceutical compositions for general use as antiemetics, gastric emptiers, selective serotonin inhibitors or modulators, antianxiety agents and antiarrhythmics of this invention comprise at least one of the compounds of Formula I, as active ingredients in an amount to provide effective antiemetic, gastric emptying or antianxiety action. Daily dosages contemplated for adult humans are in the range of 10 mcg to 100 mg, advantageously 50 mcg to 50 mg and unit dosage forms contain of the order of 1 mcg to 50 mg, preferably about 5 mcg to 25 mg of the more active Formula I compounds. However the scope of the invention is not limited by these contemplations due to uncertainty in transposing from animal data to humans. The compounds are thus presented in a therapeutic composition suitable for oral, parenteral, subcutaneous, intramuscular, intraperitoneal or intravenous administration. Thus, for example compositions for oral administration can take the form of elixirs, capsules, tablets or coated tablets containing carriers conveniently used in the pharmaceutical art. Exemplary of solid carriers including tableting and capsulating excipients are lactose, sucrose, potato and maize starches, talc, gelatin, agar, pectin or acacia, stearic and silicic acids, magnesium stearate, terra alba and polyvinyl pyrrolidone.

For parenteral administration, the carrier or excipient can be comprised of a sterile parenterally acceptable liquid; e.g., water or arachis oil contained in ampoules.

As stated above, co-formulation of anticancer drugs and compounds of Formula I are within the scope of this invention and it is only necessary that the active ingredient of Formula I constitute an effective amount.

The compounds of Formula I are expected to be also effective in controlling emesis caused by radiation sickness, in which use required dosages and regimen is anticipated to be about the same as for treatment of emesis due to administration of anticancer drugs.

In all of the above, it is only necessary that a suitable effective dosage will be consistent with the dosage form employed. The exact individual dosages, as well as daily dosages, will of course be determined according to standard medical principles under the direction of a physician or veterinarian.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention, and it is therefore understood that the invention is to be limited only by the scope of the appended claims.

What is claimed is:

1. A compound according to the formula:

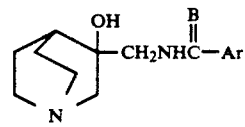

wherein B is O or S and Ar is selected from:

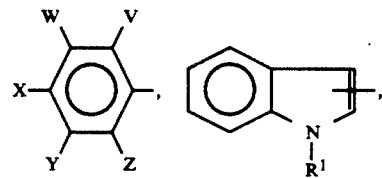

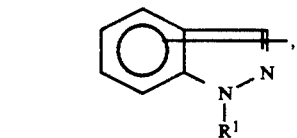

and $R^1$ is H or loweralkyl;

V is selected from hydrogen, hydroxy, —$OR^3$, —$SR^3$ or halogen;

W is selected from hydrogen and —OR³

X is selected from hydrogen, amino, loweralkylamino, diloweralkylamino, loweralkylcarbonylamino, loweralkylsulfonylamino, —OR³;

Y is selected from hydrogen, halogen, or —OR³;

Z is selected from hydrogen, halogen, or —OR³;

R³ is selected from loweralkyl, loweralkoxyloweralkyl, loweralkylthioloweralkyl, loweralkylsulfinyloweralkyl, loweralkylsulfonylloweralkyl, loweralkenyl, 2-tetrahydropyranylmethyl, substituted benzyl, diloweralkylaminocarbonylloweralkyl; the N-oxide or a pharmaceutically acceptable salt thereof.

2. A compound according to claim 1 wherein the compound is selected from the group consisting of:
5-chloro-N-(3-hydroxy-1-azabicyclo[2.2.2]oct-3-ylmethyl)-2-methoxy-4-(methylamino)benzamide,
4-amino-5-chloro-N-(3-hydroxy-1-azabicyclo[2.2.2]oct-3-ylmethyl)-2-methoxybenzamide,
N-(3-hydroxy-1-azabicyclo[2.2.2]oct-3-ylmethyl)-1H-indole-3-carboxamide,
4-amino-5-chloro-2-hydroxy-N-(3-hydroxy-1-azabicyclo-2.2.2]oct-3-ylmethyl)benzamide,
4-amino-5-chloro-N-(3-hydroxy-1-azabicyclo[2.2.2]oct-3-ylmethyl)-2-(2-methoxyethoxy)benzamide,
5-chloro-N-(3-hydroxy-1-azabicyclo[2.2.2]oct-3-ylmethyl)-2-methoxy-4-[(methylsulfonyl)amino]benzamide,
N-(3-hydroxy-1-azabicyclo[2.2.2]oct-3-ylmethyl)-1-methylindole-3-carboxamide,
N-(3-hydroxy-1-azabicyclo[2.2.2]oct-3-ylmethyl)-1-methyl-1H-indazole-3-carboxamide, and
N-(3-hydroxy-1-azabicyclo[2.2.2]oct-3-ylmethyl)-4-[(methylsulfonyl)amino]benzamide.

3. A method of treating warm blooded animals to increase gastric emptying which comprises administering thereto a therapeutically effective amount of a compound according to the formula:

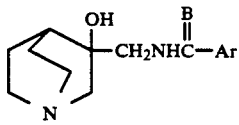

wherein B is O or S and Ar is selected from:

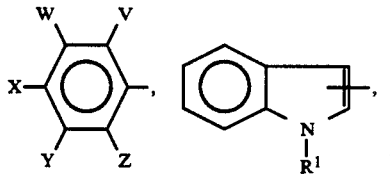

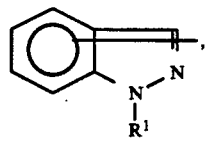

and

R¹ is H or loweralkyl;

V is selected from hydrogen, hydroxy, —OR³, —SR³ or halogen;

W is selected from hydrogen and —OR³

X is selected from hydrogen, amino, loweralkylamino, diloweralkylamino, loweralkylcarbonylamino, loweralkylsulfonylamino, —OR³;

Y is selected from hydrogen, halogen, or —OR³;

Z is selected from hydrogen, halogen, or —OR³;

R³ is selected from loweralkyl, loweralkoxyloweralkyl, loweralkylthioloweralkyl, loweralkylsulfinyloweralkyl, loweralkysulfonylloweralkyl, loweralkenyl, 2-tetrahydropyranylmethyl, substituted benzyl, diloweralkylaminocarbonylloweralkyl; the N-oxide or a pharmaceutically acceptable salt thereof.

4. The method according to claim 3 wherein the compound used is selected from the group consisting of:
5-chloro-N-(3-hydroxy-1-azabicyclo[2.2.2]oct-3-ylmethyl)-2-methoxy-4-(methylamino)benzamide,
4-amino-5-chloro-N-(3-hydroxy-1-azabicyclo[2.2.2]oct-3-ylmethyl)-2-methoxybenzamide,
N-(3-hydroxy-1-azabicyclo[2.2.2]oct-3-ylmethyl)-1H-indole-3-carboxamide,
4-amino-5-chloro-2-hydroxy-N-(3-hydroxy-1-azabicyclo-2.2.2]oct-3-ylmethyl)benzamide,
4-amino-5-chloro-N-(3-hydroxy-1-azabicyclo[2.2.2]oct-3-ylmethyl)-2-(2-methoxyethoxy)benzamide,
5-chloro-N-(3-hydroxy-1-azabicyclo[2.2.2]oct-3-ylmethyl)-2-methoxy-4-[(methylsulfonyl)amino]benzamide,
N-(3-hydroxy-1-azabicyclo[2.2.2]oct-3-ylmethyl)-1-methylindole-3-carboxamide,
N-(3-hydroxy-1-azabicyclo[2.2.2]oct-3-ylmethyl)-1-methyl-1H-indazole-3-carboxamide, and
N-(3-hydroxy-1-azabicyclo[2.2.2]oct-3-ylmethyl)-4-[(methylsulfonyl)amino]benzamide.

5. A method of treating emesis in warm-blooded animals which comprises administering thereto a therapeutically effective amount of a compound according to the formula:

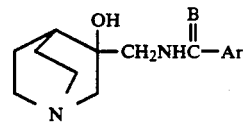

wherein B is O or S and Ar is selected from:

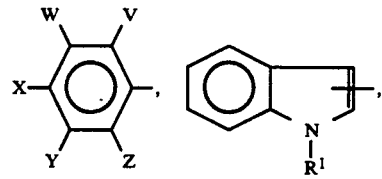

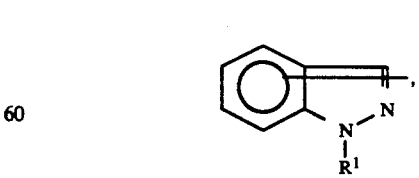

and

R¹ is H or loweralkyl;

V is selected from hydrogen, hydroxy, —OR³, —SR³ or halogen;

W is selected from hydrogen and —OR³

X is selected from hydrogen, amino, loweralkylamino, diloweralkylamino, loweralkylcarbonylamino, loweralkylsulfonylamino, —OR³;
Y is selected from hydrogen, halogen, or —OR³;
Z is selected from hydrogen, halogen, or —OR³;
R³ is selected from loweralkyl, loweralkoxyloweralkyl, loweralkylthioloweralkyl, loweralkylsulfinylloweralkyl, loweralkylsulfonylloweralkyl, loweralkenyl, 2-tetrahydropyranylmethyl, substituted benzyl, diloweralkylaminocarbonylloweralkyl; the N-oxide or a pharmaceutically acceptable salt thereof.

6. The method according to claim 5 wherein the compound used is selected from the group consisting of:
5-chloro-N-(3-hydroxy-1-azabicyclo[2.2.2]oct-3-ylmethyl)-2-methoxy-4-(methylamino)benzamide,
4-amino-5-chloro-N-(3-hydroxy-1-azabicyclo[2.2.-2]oct-3-ylmethyl)-2-methoxybenzamide,
N-(3-hydroxy-1-azabicyclo[2.2.2]oct-3-ylmethyl)-1H-indole-3-carboxamide,
4-amino-5-chloro-2-hydroxy-N-(3-hydroxy-1-azabicyclo-2.2.2]oct-3-ylmethyl)benzamide,
4-amino-5-chloro-N-(3-hydroxy-1-azabicyclo[2.2.-2]oct-3-ylmethyl)-2-(2-methoxyethoxy)benzamide,
5-chloro-N-(3-hydroxy-1-azabicyclo[2.2.2]oct-3-ylmethyl)-2-methoxy-4-[(methylsulfonyl)amino]benzamide,
N-(3-hydroxy-1-azabicyclo[2.2.2]oct-3-ylmethyl)-1-methylindole-3-carboxamide,
N-(3-hydroxy-1-azabicyclo[2.2.2]oct-3-ylmethyl)-1-methyl-1H-indazole-3-carboxamide, and
N-(3-hydroxy-1-azabicyclo[2.2.2]oct-3-ylmethyl)-4-[(methylsulfonyl)amino]benzamide.

7. A method of treating anxiety in warm-blooded animals which comprises administering thereto a therapeutically effective amount of a compound according to the formula:

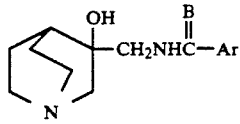

wherein B is O or S and Ar is selected from:

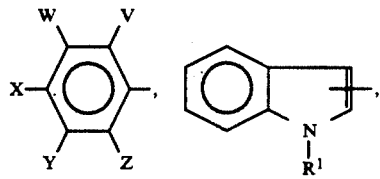

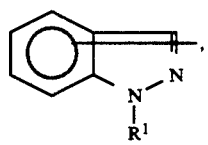

and
R¹ is H or loweralkyl;
V is selected from hydrogen, hydroxy, —OR³, —SR³ or halogen;
W is selected from hydrogen and —OR³

X is selected from hydrogen, amino, loweralkylamino, diloweralkylamino, loweralkylcarbonylamino, loweralkylsulfonylamino, —OR³;
Y is selected from hyrogen, halogen, or —OR³;
Z is selected from hydrogen, halogen, or —OR³;
R³ is selected from loweralkyl, loweralkoxyloweralkyl, loweralkylthioloweralkyl, loweralkylsulfinylloweralkyl, loweralkylsulfonylloweralkyl, loweralkenyl, 2-tetrahydropyranylmethyl, substituted benzyl, diloweralkylaminocarbonylloweralkyl; the N-oxide or a pharmaceutically acceptable salt thereof.

8. The method according to claim 7 wherein the compound used is selected from the group consisting of:
5-chloro-N-(3-hydroxy-1-azabicyclo[2.2.2]oct-3-ylmethyl)-2-methoxy-4-(methylamino)benzamide,
4-amino-5-chloro-N-(3-hydroxy-1-azabicyclo[2.2.-2]oct-3-ylmethyl)-2-methoxybenzamide,
N-(3-hydroxy-1-azabicyclo[2.2.2]oct-3-ylmethyl)-1H-indole-3-carboxamide,
4-amino-5-chloro-2-hydroxy-N-(3-hydroxy-1-azabicyclo-2.2.2]oct-3-ylmethyl)benzamide,
4-amino-5-chloro-N-(3-hydroxy-1-azabicyclo[2.2.-2]oct-3-ylmethyl)-2-(2-methoxyethoxy)benzamide,
5-chloro-N-(3-hydroxy-1-azabicyclo[2.2.2]oct-3-ylmethyl)-2-methoxy-4-[(methylsulfonyl)amino]benzamide,
N-(3-hydroxy-1-azabicyclo[2.2.2]oct-3-ylmethyl)-1-methylindole-3-carboxamide,
N-(3-hydroxy-1-azabicyclo[2.2.2]oct-3-ylmethyl)-1-methyl-1H-indazole-3-carboxamide, and
N-(3-hydroxy-1-azabicyclo[2.2.2]oct-3-ylmethyl)-4-[(methylsulfonyl)amino]benzamide.

9. A method of treating a warm-blooded animal to enhance cognitive function which comprises administering thereto a therapeutically effective amount of a compound according to the formula:

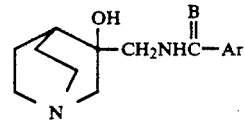

wherein B is O or S and Ar is selected from:

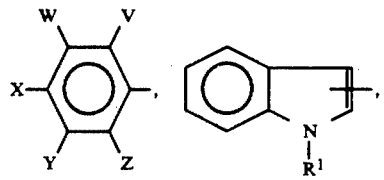

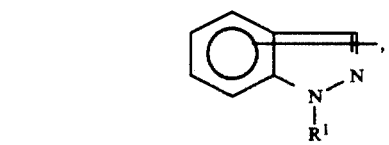

and
R¹ is H or loweralkyl;
V is selected from hydrogen, hydroxy, —OR³, —SR³ or halogen;
W is selected from hydrogen and —OR³

X is selected from hydrogen, amino, loweralkylamino, diloweralkylamino, loweralkylcarbonylamino, loweralkylsulfonylamino, —OR³;
Y is selected from hydrogen, halogen, or —OR³;
Z is selected from hydrogen, halogen, or —OR³;
R³ is selected from loweralkyl, loweralkoxyloweralkyl, loweralkylthioloweralkyl, loweralkylsulfinylloweralkyl, loweralkylsulfonylloweralkyl, loweralkenyl, 2-tetrahydropyranylmethyl, substituted benzyl, diloweralkylaminocarbonylloweralkyl; the N-oxide or a pharmaceutically acceptable salt thereof.

10. The method according to claim 9 wherein the compound used is selected from the group consisting of:
5-chloro-N-(3-hydroxy-1-azabicyclo[2.2.2]oct-3-ylmethyl)-2-methoxy-4-(methylamino)benzamide,
4-amino-5-chloro-N-(3-hydroxy-1-azabicyclo[2.2.2]oct-3-ylmethyl)-2-methoxybenzamide,
N-(3-hydroxy-1-azabicyclo[2.2.2]oct-3-ylmethyl)-1H-indole-3-carboxamide,
4-amino-5-chloro-2-hydroxy-N-(3-hydroxy-1-azabicyclo-2.2.2]oct-3-ylmethyl)benzamide,
4-amino-5-chloro-N-(3-hydroxy-1-azabicyclo[2.2.2]oct-3-ylmethyl)-2-(2-methoxyethoxy)benzamide,
5-chloro-N-(3-hydroxy-1-azabicyclo[2.2.2]oct-3-ylmethyl)-2-methoxy-4-[(methylsulfonyl)amino]benzamide,
N-(3-hydroxy-1-azabicyclo[2.2.2]oct-3-ylmethyl)-1-methylindole-3-carboxamide,
N-(3-hydroxy-1-azabicyclo[2.2.2]oct-3-ylmethyl)-1-methyl-1H-indazole-3-carboxamide, and
N-(3-hydroxy-1-azabicyclo[2.2.2]oct-3-ylmethyl)-4-[(methylsulfonyl)amino]benzamide.

11. A method of inhibiting or modulating certain effects of serotonin in warm-blooded animals which comprises administering thereto a therapeutically effective amount of a compound according to the formula:

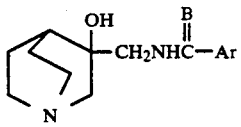

wherein B is O or S and Ar is selected from:

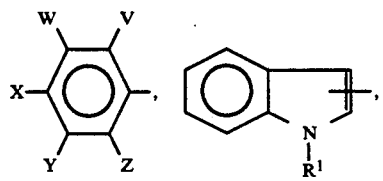

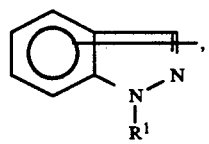

and
R¹ is H or loweralkyl;
V is selected from hydrogen, hydroxy, —OR³, —SR³ or halogen;
W is selected from hydrogen and —OR³

X is selected from hydrogen, amino, loweralkylamino, diloweralkylamino, loweralkylcarbonylamino, loweralkylsulfonylamino, —OR³;
Y is selected from hydrogen, halogen, or —OR³;
Z is selected from hydrogen, halogen, or —OR³;
R³ is selected from loweralkyl, loweralkoxyloweralkyl, loweralkylthioloweralkyl, loweralkylsulfinylloweralkyl, loweralkylsulfonylloweralkyl, loweralkenyl, 2-tetrahydropyranylmethyl, substituted benzyl, diloweralkylaminocarbonylloweralkyl; the N-oxide or a pharmaceutically acceptable salt thereof.

12. The method according to claim 11 wherein the compound used is selected from the group consisting of:
5-chloro-N-(3-hydroxy-1-azabicyclo[2.2.2]oct-3-ylmethyl)-2-methoxy-4-(methylamino)benzamide,
4-amino-5-chloro-N-(3-hydroxy-1-azabicyclo[2.2.-2]oct-3-ylmethyl)-2-methoxybenzamide,
N-(3-hydroxy-1-azabicyclo[2.2.2]oct-3-ylmethyl)-1H-indole-3-carboxamide,
4-amino-5-chloro-2-hydroxy-N-(3-hydroxy-1-azabicyclo-2.2.2]oct-3-ylmethyl)benzamide,
4-amino-5-chloro-N-(3-hydroxy-1-azabicyclo[2.2.-2]oct-3-ylmethyl)-2-(2-methoxyethoxy)benzamide,
5-chloro-N-(3-hydroxy-1-azabicyclo[2.2.2]oct-3-ylmethyl)-2-methoxy-4-[(methylsulfonyl)amino]benzamide,
N-(3-hydroxy-1-azabicyclo[2.2.2]oct-3-ylmethyl)-1-methylindole-3-carboxamide,
N-(3-hydroxy-1-azabicyclo[2.2.2]oct-3-ylmethyl)-1-methyl-1H-indazole-3-carboxamide, and
N-(3-hydroxy-1-azabicyclo[2.2.2]oct-3-ylmethyl)-4-[(methylsulfonyl)amino]benzamide.

13. A pharmaceutical composition comprised of:
a. an effective amount of a compound for increasing gastric emptying, reducing emesis, reducing anxiety, and treating disorders due to serotonin imbalance according to the formula:

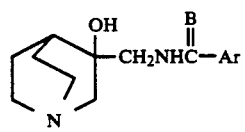

wherein B is O or S and Ar is selected from:

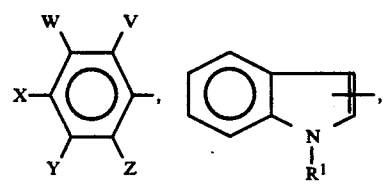

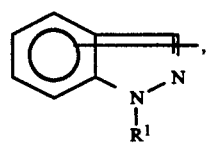

and
R¹ is H or loweralkyl;
V is selected from hydrogen, hydroxy, —OR³, —SR³ or halogen;
W is selected from hydrogen and —OR³

X is selected from hydrogen, amino, loweralkylamino, diloweralkylamino, loweralkylcarbonylamino, loweralkylsulfonylamino, —OR$^3$;
Y is selected from hydrogen, halogen, or —OR$^3$;
Z is selected from hydrogen, halogen, or —OR$^3$;
R$^3$ is selected from loweralkyl, loweralkoxyloweralkyl, loweralkylthioloweralkyl, loweralkylsulfinylloweralkyl, loweralkylsulfonylloweralkyl, loweralkenyl, 2-tetrahydropyranylmethyl, substituted benzyl, diloweralkylaminocarbonylloweralkyl; the N-oxide or a pharmaceutically acceptable salt thereof, and b. a pharmaceutical carrier.

* * * * *